(12) United States Patent
Hauger et al.

(10) Patent No.: US 7,488,070 B2
(45) Date of Patent: Feb. 10, 2009

(54) OPTICAL MEASURING SYSTEM AND OPTICAL MEASURING METHOD

(75) Inventors: Christoph Hauger, Aalen (DE); Peter Reimer, Ellwangen (DE)

(73) Assignee: Carl Zeiss AG, Oberkochen (DE)

( * ) Notice: Subject to any disclaimer, the term of this patent is extended or adjusted under 35 U.S.C. 154(b) by 0 days.

(21) Appl. No.: 11/472,030

(22) Filed: Jun. 21, 2006

(65) Prior Publication Data

US 2007/0013918 A1    Jan. 18, 2007

Related U.S. Application Data

(63) Continuation of application No. PCT/EP04/14636, filed on Dec. 22, 2004.

(30) Foreign Application Priority Data

Dec. 22, 2003    (DE)    ............................... 103 60 570

(51) Int. Cl.
*A61B 3/00* (2006.01)
*A61B 3/10* (2006.01)
(52) U.S. Cl. .................. 351/200; 351/216; 351/221
(58) Field of Classification Search ................ 359/811, 359/819, 820, 821, 822, 823, 813
See application file for complete search history.

(56) References Cited

U.S. PATENT DOCUMENTS 5,321,501 A    6/1994    Swanson et al.

(Continued)

FOREIGN PATENT DOCUMENTS

DE    101 57 842 A1    6/2003

(Continued)

OTHER PUBLICATIONS

Roorda, A., et al., "Adaptive Optics Scanning Laser Opthalmoscopy", Optics Express, vol. 10, No. 9, May 6, 2002, pp. 405-412.

(Continued)

*Primary Examiner*—Ricky L Mack
*Assistant Examiner*—Brandi N Thomas
(74) *Attorney, Agent, or Firm*—Potomac Patent Group PLLC

(57) ABSTRACT

An optical measuring system, including at least one radiation source; a first beam splitter; a second beam splitter; an OCT detector; a wavefront detector which is different from the OCT detector; at least one active optical element; and a collimator. The radiation source, the first beam splitter, the second beam splitter, the OCT detector, the wavefront detector, the at least one active optical element, and the collimator are arranged such that a source beam generated by the at least one radiation source is divided into an object illuminating beam and a reference beam by the first beam splitter; the object illuminating beam is directed by the collimator to an object position via the at least one active optical element; radiation emanating from the object position is formed to an object measuring beam by at least the collimator; the object measuring beam is directed to the second beam splitter via the at least one active optical element; the object measuring beam is divided into an OCT measuring beam and a wavefront measuring beam by the second beam splitter; the wavefront measuring beam is directed to the wavefront detector; the OCT measuring beam is directed to the OCT detector; and the reference beam is directed to the OCT detector.

20 Claims, 3 Drawing Sheets

U.S. PATENT DOCUMENTS

| | | | |
|---|---|---|---|
| 6,307,634 | B2 | 10/2001 | Hitzenberger et al. |
| 6,579,282 | B2 * | 6/2003 | Bille et al. .................... 606/5 |
| 6,588,900 | B1 | 7/2003 | Le Gargasson et al. |
| 2002/0001088 | A1 * | 1/2002 | Wegmann et al. ........... 356/521 |
| 2002/0097376 | A1 | 7/2002 | Applegate et al. |
| 2003/0053026 | A1 | 3/2003 | Roorda |
| 2003/0107744 | A1 | 6/2003 | Hauger |

FOREIGN PATENT DOCUMENTS

| | | |
|---|---|---|
| DE | 101 57 942 A1 | 6/2003 |
| DE | 600 00 827 T2 | 10/2003 |
| WO | WO 98/27863 | 7/1998 |

OTHER PUBLICATIONS

Miller, D.T., "VisionScienceList: Postdoc in Biomedical Optics", Indiana University, Postdoctoral Fellow Posting, www.visionscience.com/mail/vslist, Oct. 1999, pp. 1-3.

"Annual Report, Program Year 2, Reporting from Nov. 1, 2000 to Oct. 31, 2001", National Science Foundation, Center for Adaptive Optics, University of California, Santa Cruz, Chapter 2.1.8 Indiana University's Progress on the Coherence-Gated Retinal Camera, p. 29; Chapter 2.1.9 LLNL Adaptive Optics Phoropter, p. 30.

Zvyagin, A.V., et al., "Achromatic Optical Phase Shifter-Modulator", Optics Letters, vol. 26, No. 4, Feb. 15, 2001, pp. 187-189.

Hauger, C., et al., "Interferometer for Optical Coherence Tomography", Applied Optics, vol. 42, No. 19, Jul. 1, 2003, pp. 3896-3902.

Tearney, G.J., et al., "High-speed Phase- and Group-delay Scanning with a Grating-based Phase Control Delay Line", Optics Letters, vol. 22, No. 23, Dec. 1, 1997, pp. 1811-1813.

Paterson, C., et al., "Hybrid Curvature and Gradient Wave-front Sensor", Optics Letters, vol. 25, No. 23, Dec. 1, 2000, pp. 1687-1689.

Munro, I., et al., "A High Bandwidth Breadboard System to Investigate Adaptive Optics in the Human Eye", pp. 1-7.

Stone, J.A., et al., "Diode Lasers in Length Metrology: Application to Absolute Distance Interferometry", Cal Lab The International Journal of Metrology, Nov./Dec. 1999, pp. 1-7.

* cited by examiner

OPTICAL MEASURING SYSTEM AND OPTICAL MEASURING METHOD

This application is a continuation of International Application No. PCT/EP2004/014636 filed Dec. 22, 2004, which claims priority and benefit from German patent application No. 103 60 570.3, filed Dec. 22, 2003, the entire teachings of both of these documents are incorporated herein by reference.

BACKGROUND OF THE INVENTION

1. Field of the Invention

Present invention relates to an optical measuring system and an optical measuring method.

In particular, the measuring system and the measuring method can be used for examining a retina of an eye of a patient, and for creating a data set, from which images of the retina can be created. The data set can, in particular, be two-dimensional or three-dimensional.

2. Brief Description of Related Art

From U.S. Pat. No. 5,321,501, an optical measuring system for the examination of a retina of an eye is known. The disclosure of this document is fully incorporated by reference into the present application.

From pages 29 and 30 of the Program Year 2 of the Annual Report of the National Science Foundation, Center for Adaptive Optics, University of California, Santa Cruz, Calif., a retina camera is known, which is subsequently discussed in conjunction with FIG. 1.

The camera 1 serves to take images of a retina 3 of an eye 5 of a patient. The camera 1 operates according to an OCT-method, wherein OCT stands for "Optical Coherence Tomography". Two light sources 7 and 9 are provided for selectively or together creating a source beam 11, which is divided into an object illuminating beam 15 and a reference beam 17 by a first beam splitter 13. The reference beam 17 is reflected back into itself at an actuator-mirror-unit 19, wherein an optical path length of the reference beam between the beam splitter 13 and its reflection at the actuator-mirror-unit 19 is variable via an actuator of the unit 19. The object illuminating beam 15 is focussed onto the retina 3 by a lens 21 of the eye 5, and light of the object illuminating beam reflected or scattered back from the retina 3 is again incident on the beam splitter 13 and is transmitted therethrough. The light of the reference beam reflected off the actuator-mirror-unit 19 is reflected at the beam splitter 13 and is superimposed with the light coming back from the retina, to form a common light beam 22. The light beam 22 is directed via lenses 25 to an active optical element 27 and reflected therefrom. The reflected beam 22 is directed via a further lens 29 and a mirror 30 to a second beam splitter 33. The beam splitter 33 divides beam 22 into an OCT measuring beam 35 and a wavefront measuring beam 37. The OCT measuring beam 35 is directed via lenses 39 onto a camera 49, which obtains OCT measuring data from a depth of the retina 3 set by actuating the actuator-mirror-unit 19.

The wavefront measuring beam 37 is directed to a Hartmann-Shack wavefront sensor 41 via a lens 39, to detect wavefronts in the beam 22. The active optical element 27 is actuated in dependence of the detected wavefronts in order to improve on a quality of the OCT images obtained by the detector 49.

It has been found that this conventional system does not fulfill expectations with regard to its imaging quality, in particular with respect to its lateral and depth resolution.

SUMMARY OF THE INVENTION

Accordingly, it is an object of the present invention to provide an optical measuring system and an optical measuring method, in particular for measuring a retina of an eye, which compared to the conventional measuring system has an improved imaging quality.

Under a first aspect, the invention provides an optical measuring system, which comprises a radiation source, a first beam splitter, a second beam splitter, an OCT detector, a wavefront detector, at least one active optical element and a collimator. These components are arranged into an optical circuitry in such a manner, that a source beam to be generated by the radiation source is divided by the first beam splitter into an object illuminating beam and a reference beam; the object illuminating beam is directed via the at least one active optical element through the collimator to an object position, radiation emanating from the object position is formed by the collimator into an object measurement beam; the object measurement beam is directed via the at least one active optical element to the second beam splitter; the object measurement beam is divided into an OCT measurement beam and a wavefront measurement beam by the second beam splitter; the wavefront measurement beam is directed to the wavefront detector; the OCT measurement beam is directed to the OCT detector; and the reference beam is directed to the OCT detector.

In the measuring system according to the invention, the at least one active optical element may be controlled in dependence of a measurement signal provided by the wavefront detector, to improve on a quality of the measurement signal provided by the OCT detector. This results in an improvement on the data obtained from the object by the system. Herein, and in contrast to the conventional system, both the object measurement beam and the wavefront measurement beam are directed via the active optical element, whereas the light of the reference beam is not directed via the active optical element in its path to the OCT detector. Such an active optical element is commonly termed an adaptive optical element, and optics containing such an element are termed adaptive optics.

According to a preferred embodiment, the active optical element is set such that the wavefronts detected by the wavefront detector are substantially planar wavefronts.

The active optical element has an extended cross section, within which the beam directed via the active optical element interacts with same. Herein, the active optical element is adapted to provide for the beam variable optical path lengths position-dependent within the cross section.

The active optical element may operate in reflection, i.e. it reflects the beam directed to it, or in transmission, i.e. it transmits the beam directed through it.

According to an exemplary embodiment a first scanner is provided, to move a position at which the object illuminating beam is incident on the object, in a direction transverse to the direction of the incident object illuminating beam. Herein, the first scanner may be pivotable in two directions in order to allow for two-dimensional scanning of the object.

According to an exemplary embodiment, the active optical element is used as the first scanner.

According to a further exemplary embodiment a second scanner is provided, for changing an optical path length of the reference beam between the first beam splitter and the OCT detector. Thereby, the object can be scanned according to the OCT method in its depth, i.e. in the direction of the incident object illuminating beam.

According to an exemplary embodiment, the wavefront sensor is a Hartmann sensor or a Hartmann-Shack sensor.

According to a further exemplary embodiment, the object position, i.e. the position at which the object illuminating beam is focussed in the object, can also be moved in the beam direction of the illuminating beam, for moving that region of the object, from which OCT data are acquired, in the depth direction of the object.

According to an exemplary embodiment, to achieve this the collimator is variable, for example by translation in the direction of the object illuminating beam.

According to a further exemplary embodiment, the at least one active optical element is controlled to having a focussing or defocussing effect on the illuminating light beam.

According to a further aspect of the invention, there is provided an optical measuring method, comprising performing at least one OCT measurement on an object to be examined, and performing at least one wavefront measurement. The OCT measurement is made by generating object illuminating light, sending a first portion of the object illuminating light to the object, and interferingly superimposing at least portion of object measurement light emanating from the object with a second portion of the object illuminating light. Performing the at least one wavefront measurement is made with at least a portion of the measurement light emanating from the object.

Furthermore, to improve on a quality of the performed measurement, optical path lengths of a beam formed by the object illuminating light between its generation and the object are changed, wherein this change is made position-dependent across a cross section of the beam and in dependence of the at least one wavefront measurement. Similarly, optical path lengths of a second beam formed by the object measurement light between the object and the interferent superposition are changed.

According to an exemplary embodiment, first the at least one wavefront measurement is performed, and in dependence thereof, a setting of the optical path lengths of the first and second beam is performed. Then, a plurality of OCT measurements is carried out, in each of which the object illuminating light is focussed at a different small region of the object. Thereby, OCT measurement data can quickly be obtained from an extended region of the object, at an unchanged setting of the optical path lengths of the first and second beam.

According to a further exemplary embodiment, it is envisaged to move a window in which measurement data is acquired, laterally to a propagation direction of the object illuminating light, after acquisition of measurement data in said window, and to anew acquire OCT measurement data in the moved window, but to beforehand perform a further wavefront measurement for carrying out suitable settings of the optical path lengths of the first and second beam for the moved window.

BRIEF DESCRIPTION OF THE DRAWINGS

In the following, exemplary embodiments of the present invention are explained in further details with reference to the figures, wherein.

DETAILED DESCRIPTION OF EXEMPLARY EMBODIMENTS

Figure 2:
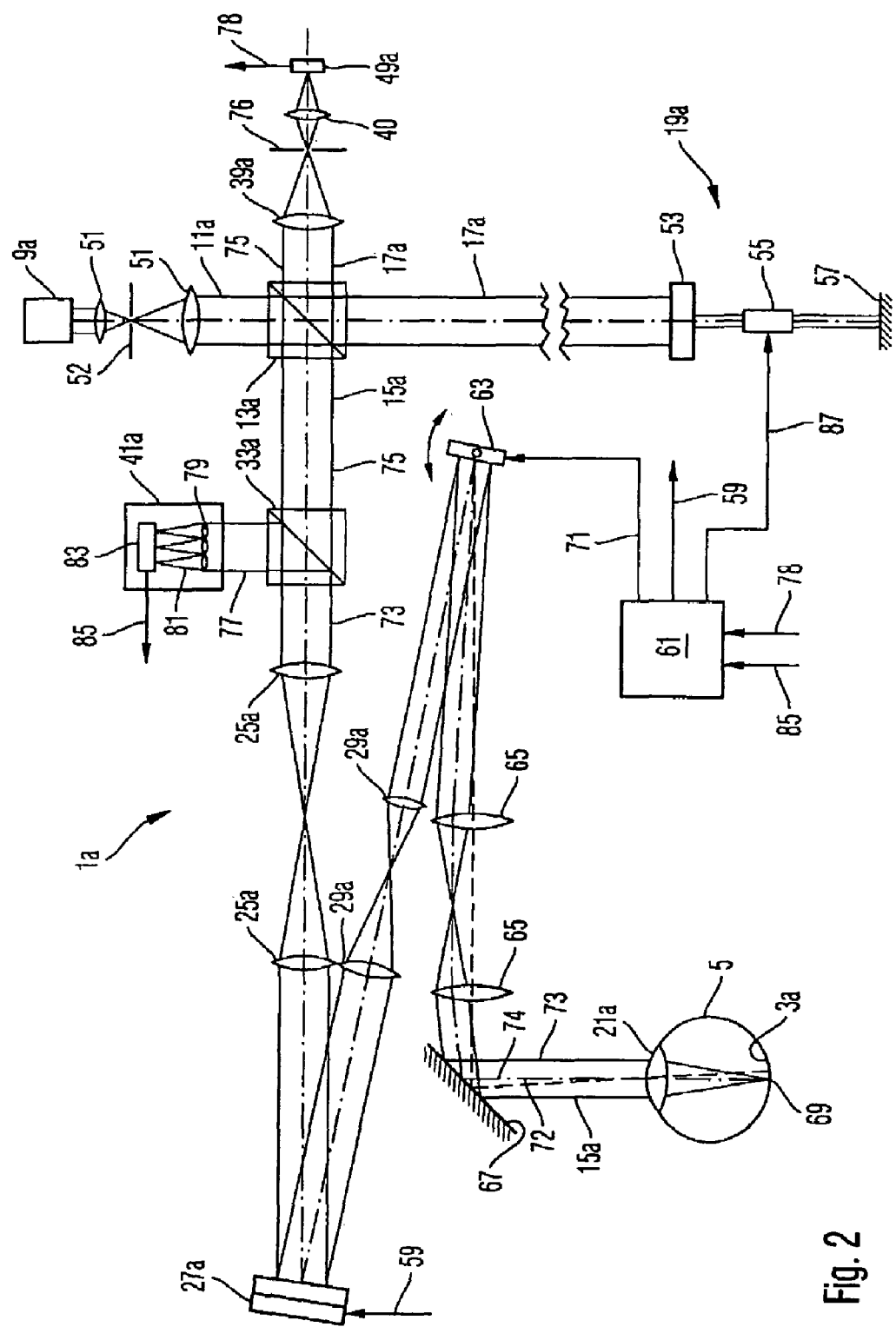
FIG. 2 shows an arrangement of an optical measuring system according to an embodiment of the invention.

In FIG. 2, an embodiment of an optical measurement system according to the present invention is shown as a circuit scheme of an optical circuit of same.

The optical measurement system 1a comprises a radiation source 9a for generating a source beam 11a via collimating lenses 51 and a space filter 52. Herein, the radiation source 9a is a radiation source suitable to generate light with which an OCT measurement method can be performed on an object to be examined. In particular, this light is temporally incoherent, and may further also be spatially incoherent. For example, the radiation source 9a may for this purpose be a superluminescence diode. The object to be examined may be, for example, a retain 3a of an eye 5a of a patient.

Through a first beam splitter 13a, the source beam 11a is divided into a reference beam 17a and an object illuminating beam 15a. The reference beam 17a is reflected at a mirror 53 of an actuator-reflector-unit 19a, and is reflected onto itself, reflected at the first beam splitter 13a and directed onto an OCT detector 49a via a lens 39a, a confocal aperture 76 and a further lens 40. The unit 19a further comprises an actuator 55 for moving the mirror 53 relative to a basis 57, so that an optical path length of the reference beam 17a between its division at the beam splitter 13a and the mirror 53 is variable.

The object illuminating beam 15a passes through a second beam splitter 33a and is directed via lenses 25a to an active optical element 27a reflecting the object illuminating beam 15a. An example for such an active optical element is a deformable mirror as can be obtained from the company Xinetics, Inc., 37 MacArthur Ave., Devens, Mass. 01432, USA. The object illuminating beam 15a, where incident on the active optical element 27a, has an extended cross section, and the active optical element 27a is controllable via a control line 59 from the control 61, to locally deform a mirror surface provided by the active optical element 27a for the incident beam 15a.

After reflection off the active optical element 27a, the object illuminating beam 15a passes through one or more lenses 29a and is incident on a scanning mirror 63, is reflected by same, passes through a further lens optics 65, and, after reflection at a further mirror 67, enters into an eye 5a through the lens 21a of the eye 5a in such a manner, that the object illuminating beam 15a is incident on the retina 3a of the eye 5a at an object position 69. The scanning mirror 63 is controllable to two-dimensionally move the object position 69 transversely to a direction of incidence of the object illuminating beam 15a on the retina 3a.

Radiation emanating from the retina 3a at the object position 69 is formed by the eye lens 21a to an object measurement beam 73, the principal axis 74 of which substantially coincides with a principal axis 72 of the object illuminating beam 15a, so that the object measurement beam 73 is directed back to the beam splitter 33a via the mirror 67, the lens 65, the pivoting mirror 63, the lens 29a, the active optical element 27a and the lenses 25a. By the beam splitter 33a, the object measurement beam 73 is divided into an OCT measurement beam 75 and a wavefront measurement beam 77. The OCT measurement beam 75 passes through the beam splitter 13a and thereby interferingly overlaps with the reference beam 17a, so that the OCT detector 49a registers an OCT measurement signal, which is transmitted to the control 61 via a line 78.

The wavefront measurement beam 77 enters into the wavefront detector 41a, which is provided by a Hartmann sensor or a Hartmann-Shack sensor, for example. There, the wavefront measurement beam 77 is divided into a manifold of partial beams 81 by an array 79 of microlenses, wherein each partial beam 81 is focussed onto a spatially resolving detector 83. Via a line 85, an image of the detector 83 is transmitted to the control 61, which evaluates focus positions of the partial beams 81 in the detector image and, in dependence of the evaluation, controls the active optical element 27a in such a manner that wavefronts in the wavefront measurement beam 77, and therefore also in the object measurement beam 73, are substantially planar wavefronts. Thereby, wavefront aberrations due to non-perfect imaging of, e.g., the lens 21a of the eye 5a, or/and due to irregularities in the vitrious body of the eye, or/and due to a non-perfect imaging of the measuring optics in the object measurement beam 73, are compensated, so that the OCT measurement beam 75 is prepared such that its wavefronts can almost ideally interfere with wavefronts of the reference beam 17a, so that the OCT measurement signal provides a particularly good depth resolution and lateral resolution of the retina. Herein, the optical path length between the beam splitter 13a and the mirror 53 substantially corresponds to the optical path length of the object measurement beam between the object position 69 and the beam splitter 13a. Thereby, a depth resolution of, e.g., 1 µm to 5 µm can be achieved.

At the same time, wavefronts of the object illuminating beam 15a are prepared by so controlling the active optical element, in such a manner that in the presence of the irregularities of the virtious body and the non-perfect imaging of the eye lens 21a, a particularly small spot on the retina 3a is illuminated at the object position 69, so that also the lateral resolution of the measurement data provided by the measuring system 1a is of a high quality. Thereby, it is possible to achieve a lateral resolution of, e.g., 1 µm to 10 µm.

An OCT measurement is performed at an object position 69, through the control 61 activating via a control line 87 the actuator 55, so that same moves the mirror 53 in a certain range, i.e. by a certain displacement, to change the optical path length of the reference beam 17a between the beam splitter 13a and the OCT detector 49a in a range corresponding to twice the displacement. During such a displacement, the control 61 reads out plural measurement values of the OCT detector 49a, wherein these measurement values correspond to detected intensities.

In conjunction with FIG. 3, in the following a method for obtaining three-dimensional measurement data from a volume portion 93 of the retina 3a is described.

Figure 1:
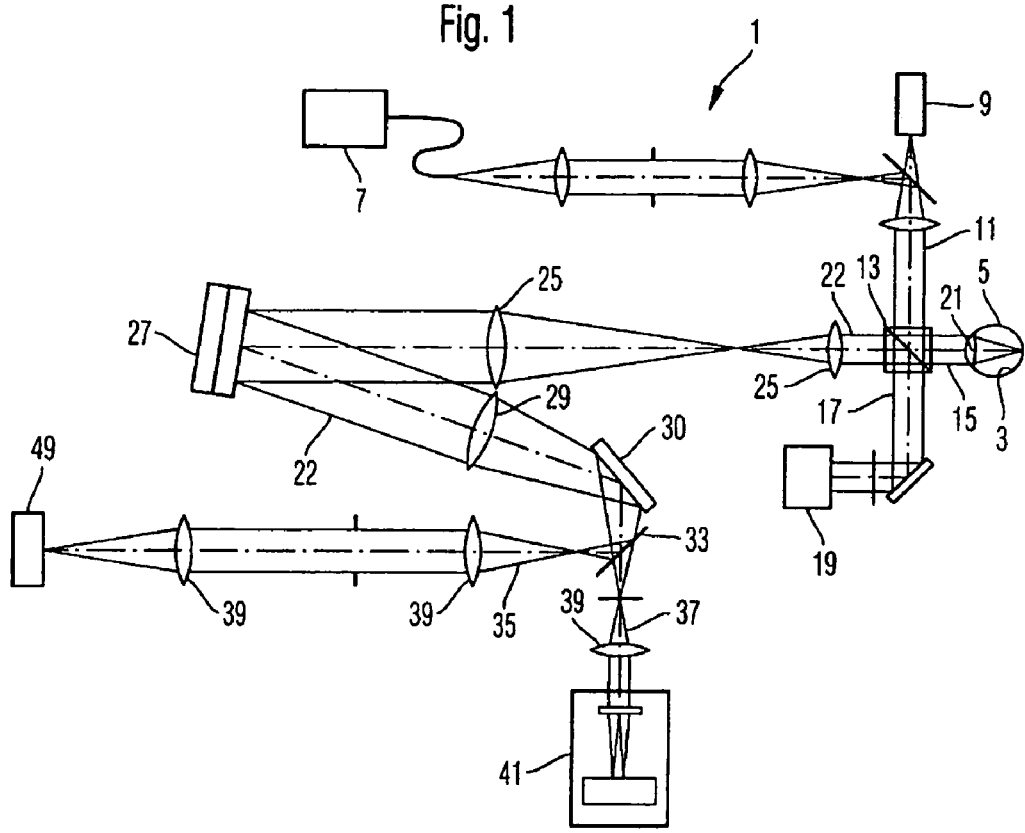
FIG. 1 shows an arrangement of a conventional optical measuring system.
Figure 3:
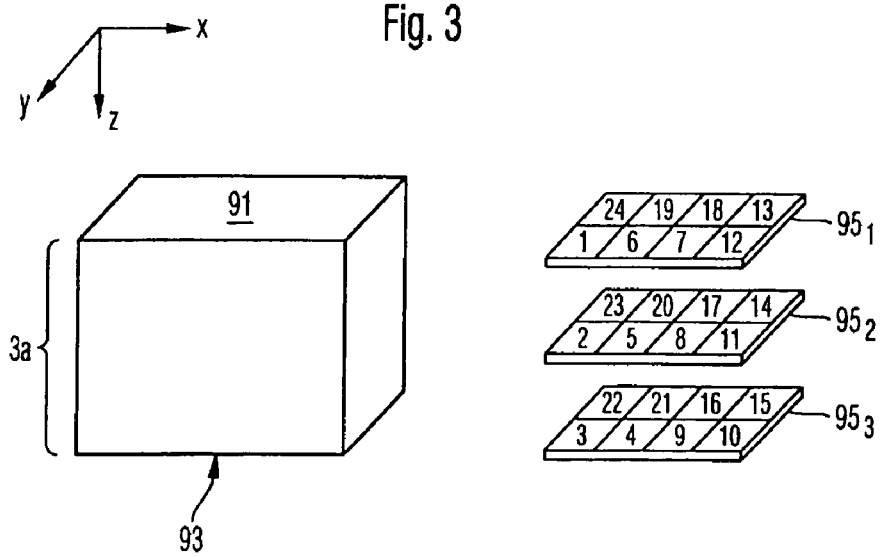
FIG. 3 shows schematically an explanation of an optical measuring method according to an embodiment of the invention.

The volume portion 93 in FIG. 3 is confined on top by a surface 91 of the retina, and extends over a length of 5 mm in x-direction and 5 mm in y-direction, wherein the x-direction and the y-direction extend transversely to the direction of the object illuminating beam 15a incident on the retina 3a. In a z-direction orthogonal to the x-direction and the y-direction, the volume portion 93 extends over 500 µm into the depth of the retina 3a.

With the method as described, measurement data from three different depths (in z-direction) are acquired. These layers are labelled $95_1$, $95_2$ and $95_3$, respectively, in FIG. 3. Each of these layers is divided in xy-direction into, e.g., eight fields or windows. Initially, the object position is moved to the center of field #1, by controlling pivoting mirror 63 and by controlling the active optical element 27a in such a manner that same provides a focussing or defocussing effect such that the focus of the object illuminating beam 15a is in the plane $95_1$ of the retina 3a. Then, the control 61 evaluates an image of the wavefront sensor 41a and thereafter sets the active optical element 27a in such a manner that the wavefronts in the OCT measurement beam 75 are substantially planar wavefronts. After this setting, the pivoting mirror 63 is controlled in such a manner that the object position 69 is sequentially located at, e.g., 25 different positions within the window #1, the 25 positions being arranged in a 5-by-5-grid. At each of the 25 positions, the object position is maintained for a time within which the actuator 55, controlled by the control 61, can perform at least one displacement, to carry out an OCT measurement with the OCT detector 49a. Thereby, within window #1 25 OCT measurement data sets are obtained.

Then, the object position is moved to the center of field #2 in plane $95_2$, by accordingly setting the pivoting mirror 69 and the focussing or defocussing effect of the active optical element 27a as described above, wherein also the actuator 55 is controlled to adapt the optical path length of the reference beam to the position of the plane $95_2$. Again, a wavefront measurement is carried out, for setting the active optical element such that for the center of window #2, the wavefronts in the OCT measurement beam 75 are substantially planar wavefronts. Then, another 25 OCT measurements are performed within the window #2.

Thereafter, corresponding measurements are carried out sequentially for fields #3 and #4 in plane $95_3$, field #5 in plane $95_2$, fields #6 and #7 in plane $95_1$, and so on.

In this manner, the measurement data for the three planes $95_1$, $95_2$ and $95_3$ can quickly be obtained. Herein, the settings of the active optical element 27a are the same for the different positions within one window, but may be different from window to window within one of the planes 95. Herein, the size of the windows can be adapted in accordance with the required accuracy to be achieved, with regard to a fast scanning of all the measurement positions within the planes.

Alternatively, it is also possible to first scan all the windows within one of the planes, and to then switch to the next plane. In the example shown in FIG. 3, the windows may be scanned in the following sequence: #1, #24, #19, #6, #7, #18, #13, #12; #11, #14, #17, #8, #5, #20, #23, #2; #3, #22, #21, #4, #16, #9, #10, #15.

In the following, variants of the embodiments described in conjunction with FIGS. 2 and 3 are explained. Components which correspond to one another with respect to their function and/or structure are labelled by corresponding numerals, which are supplemented by additional letters for discrimination.

Figure 4:
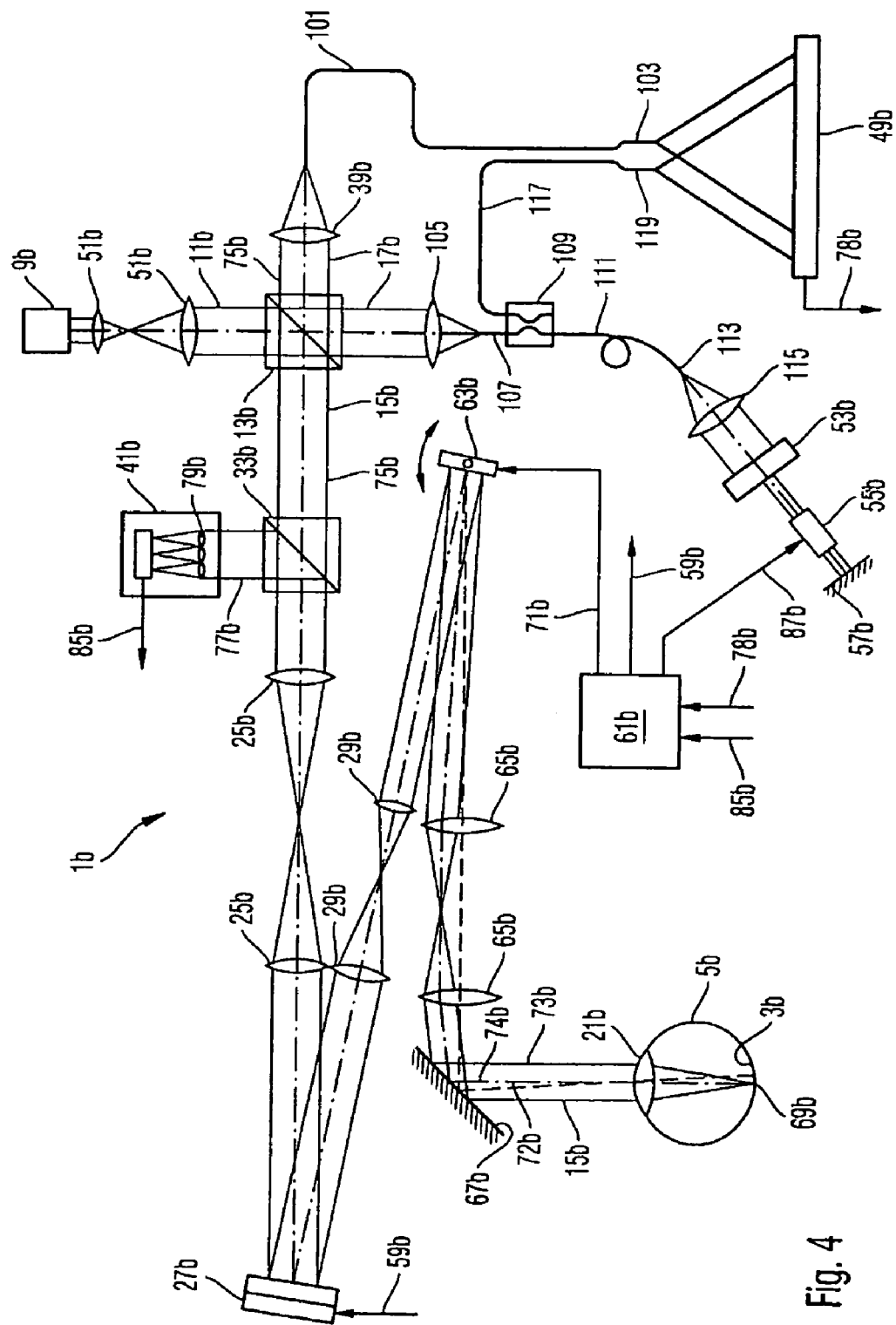
FIG. 4 shows a further embodiment of an optical measuring system according to the invention.

An optical measuring system as shown in FIG. 4 has a similar setup as the measuring system shown in FIG. 2.

An essential difference between the two measuring systems lies in the detection of the OCT measurement signal. Namely, in the measuring system 1b of FIG. 4, a source beam 11b generated by a radiation source 9b is divided by a beam splitter 13b into an object illuminating beam 15b and a reference beam 17b. A beam path of the object illuminating beam 15b between the beam splitter 13b and a retina 3b of an eye 5b is similar to the beam path shown in FIG. 2, as well as a beam path of the light emanating from the retina 3b back to the beam splitter 13b as an object measurement beam 75b. The object measurement beam 75b passes through the beam splitter 13b and is coupled into a glass fiber 101 by a collimating lens 39b, and is directed by the glass fiber 101 to a radiation exit 103, from which the light of the beam 75b is emitted onto a line detector 49b.

The reference beam 17b is coupled by a collimator 105 into a glass fiber 107, directed through a fiber coupler 109, further directed by a glass fiber 111 and emitted from the same at a fiber end 113. The emitted light is collimated by a collimator 115 and reflected at a mirror 53b. A distance of the mirror 53b from the fiber end 103 is variable by an actuator 55b, which is controlled via a line 87b. The light reflected at the mirror 53b is then coupled back into the end 103 of the fiber 111 by the collimator 115, and travels back to the fiber coupler 109, where part of its intensity is coupled into a fiber 117, from where it is emitted at a fiber end 119 towards the line detector 49b.

The two fiber ends 103 and 119 are spaced apart by a distance, so that at one site of the line detector, the optical path length in the beam path between beam splitter 13b, mirror 53b, fiber end 119 and the site on the line detector 49b is equal to the optical path length between the beam splitter 13b, via the active optical element 27b to a certain depth of the retina 3b, back via the active optical element 27b and via the end 103 of the fiber 101 to the said site on the line detector 49b, so that at this site, the interference condition is fulfilled for the respective depth of the retina. At a different site on the line detector 49b, the interference condition is fulfilled for a different depth of the retina 3b, so that by means of the line detector, a plurality of measurement data can be obtained simultaneously, whereby a particularly fast scanning of the retina 3b can be accomplished. This plurality of measurement data corresponds to the plurality of measurement data acquired in the embodiment of FIG. 2 via a displacement of the actuator.

Herein, it is also possible to provide a variable spacing between the fiber ends 103 and 119, e.g. by a drive or an actuator. By changing the distance between the fiber ends, it is then possible to change the depth range simultaneously detectable by the line detector. At a larger spacing between the fiber ends, this depth range is larger than at a smaller spacing. For example, the spacing between the fiber ends 103, 119 can be set to cover, with reference to FIG. 3, the entire depth range of the retina at once, so that in addition to the planes $95_1$, $95_2$ and $95_3$ also regions between these planes are detected. Thereby, the entire depth of the retina or part of it can be scanned, without making changes in the optical path length of the reference beam. It may, however, be advantageous in this case to set the focussing of the object illuminating beam to one of the planes $95_1$, $95_2$ and $95_3$, and to carry out the scanning of the various windows in this plane with such a focus setting. Then, the beam may be focussed to a different plane, followed by scanning of this plane. Because those planes, to which the focus has not been set, are not detected with the best attainable quality, it is possible, in order to speed up measurement, not to read out the data associated with these planes, and to restrict reading out the line detector to detector regions onto which structures of the retina are imaged, to which the object illuminating beam has been focussed.

In the embodiments described above, a single active optical element is used to change optical path lengths within the object illuminating beam and within the object measurement beam.

However, it is also possible to separate the object illuminating beam from the object measurement beam, and to direct both beams via separate, accordingly controlled active optical elements.

In the embodiments described above, a single light source is used to generate the light for the OCT measurement and the wavefront measurement. However, it is also possible to use separate light sources, which differ for example with respect to their wavelengths. The light of the two light sources may then be superposed to a common object illuminating beam.

In the embodiments described above, the beam splitter for coupling the wavefront measurement beam out of the object measurement beam is arranged in same in front of the beam splitter for dividing the beam into the object illuminating beam and the reference beam. However, it is also possible to alter the ordering of the beam splitters in the object measurement beam.

In the embodiments described above, a single pivoting mirror is provided to move the object position laterally to the direction of the object illuminating beam. However, it is also possible to use two separate mirrors, which allow for independently moving the object position in one direction each. Herein, it is also possible to provide the function of the one pivoting mirror or the other pivoting mirror by the active optical element, which is possible by accordingly controlling the active optical element.

In the embodiments described above, the focus setting of the object illuminating beam to a depth of the retina is effected by an according controlling of the active optical element. However, it is also possible to actuate other beam forming elements of the object illuminating beam for this purpose, for example by moving such elements along the direction of the object illuminating beam.

It is also envisaged to use for this purpose optical elements whose optical properties are variable by applying a control signal. An example therefore are electrically variable lenses as obtainable from, e.g., the company Varioptic, 69007 Lyon, France.

While the invention has been described also with respect to certain specific embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

The invention provides an optical measuring system and an optical measuring method, which are particularly useful for the acquisition of image data of a retina of an eye. Data acquisition is made by OCT measurements, wherein a quality of these measurement is improved by arranging an active optical element in the beam path.

What is claimed is:

1. An optical measuring system, comprising:
   at least one radiation source;
   a first beam splitter;
   a second beam splitter;
   an OCT detector;
   a wavefront detector which is different from the OCT detector;
   at least one active optical element; and
   a collimator;
   wherein the radiation source, the first beam splitter, the second beam splitter, the OCT detector, the wavefront detector, the at least one active optical element, and the collimator are arranged such that
   a source beam generated by the at least one radiation source is divided into an object illuminating beam and a reference beam by the first beam splitter;
   the object illuminating beam is directed by the collimator to an object position via the at least one active optical element;
   radiation emanating from the object position is formed to an object measuring beam by at least the collimator;

the object measuring beam is directed to the second beam splitter via the at least one active optical element;

the object measuring beam is divided into an OCT measuring beam and a wavefront measuring beam by the second beam splitter;

the wavefront measuring beam is directed to the wavefront detector;

the OCT measuring beam is directed to the OCT detector; and the reference beam is directed to the OCT detector.

2. The optical measuring system according to claim 1, further comprising a control adapted for controlling the at least one active optical element in dependence of a measurement signal provided by the wavefront detector.

3. The optical measuring system according to claim 1, further comprising a control adapted for controlling the at least one active optical element in dependence of a measurement signal provided by the wavefront detector such that wavefronts of the wavefront measuring beam at the wavefront detector are substantially plane wavefronts.

4. The optical measuring system according to claim 1, wherein the active optical element is adapted to alter an optical path length of a beam directed via the active optical element between an input cross section before interaction of the beam with the active optical element, and an output cross section after the interaction of the beam with the active optical element, position-dependent across the output cross section.

5. The optical measuring system according to claim 1, further comprising at least a first scanner for altering the object position.

6. The optical measuring system according to claim 1, further comprising a second scanner for changing an optical path length of the reference beam between the first beam splitter and the OCT detector.

7. The optical measuring system according to claim 1, wherein the wavefront detector comprises a Hartmann-Shack sensor.

8. The optical measuring system according to claim 1, wherein the OCT detector comprises a line detector.

9. The optical measuring system according to claim 1, further comprising a control adapted for controlling a refractive power of the collimator in dependence of a measurement signal provided by the OCT detector.

10. An optical measuring method, comprising:
performing at least one OCT measurement on an object to be examined, by
generating object illuminating light;
sending a first portion of the object illuminating light to the object; and
superposing a first portion of object measurement light emanating from the object with a second portion of the object illuminating light;
performing at least one wavefront measurement on a second portion of the object measurement light emanating from the object, wherein the second portion of the object measurement light is different from the first portion of the object measurement light;
changing optical path lengths of a beam formed by the object illuminating light between the generation of the object illuminating light and the object, wherein the optical path lengths are changed depending on a position across a cross section of the beam and based on the at least one wavefront measurement; and
changing optical path lengths of a second beam formed by the object measurement light between the object and the superposition of the object measurement light wherein the optical path lengths are changed depending on a position across a cross section of the beam and based on the at least one wavefront measurement.

11. The optical measuring method of claim 10, wherein a region of the first beam and a region of the second beam overlap.

12. The optical measuring method of claim 11, wherein the changing of the optical path length of the first beam and the changing of the optical path length of the second beam is performed by an active optical element positioned in the region of the first beam where same overlaps with the second beam.

13. The optical measuring method of claim 10, further comprising focussing the object measurement light in a first region of the object.

14. The optical measuring method of claim 13, further comprising moving the first region in a direction of a direction of incidence of the object measurement light on the object.

15. The optical measuring method of claim 13, further comprising moving the first region in a direction transverse to a direction of incidence of the object measurement light on the object.

16. The optical measuring method of claim 13, further comprising focussing the object illuminating light to a plurality of adjacently arranged different first regions, and performing for each of the plurality of first regions the at least one OCT measurement, without changing the optical path lengths of the first and second beam, after performing the at least one wavefront measurement and changing the optical path lengths of the first and second beams based on the at least one wavefront measurement.

17. The optical measuring method of claim 16, wherein the plurality of adjacently arranged different first regions are arranged within a second contiguous region of the object, wherein the second region is larger than the first regions.

18. The optical measuring method of claim 17, wherein the at least one wavefront measurement and the focussing to the first regions are repeatedly performed for a plurality of the second contiguous regions which mutually overlap at most partially.

19. The optical measuring method of claim 16, further comprising moving the first region in a direction of a direction of incidence of the object measurement light on the object, wherein the moving of the first region in the direction of incidence is made before performing the at least one wavefront measurement and is substantially not made between focussings of the object illuminating light to the different first regions.

20. The optical measuring system according to claim 1, wherein the at least one radiation source comprises separate light sources differing with respect to their wavelengths.

* * * * *

UNITED STATES PATENT AND TRADEMARK OFFICE
CERTIFICATE OF CORRECTION

| | |
|---|---|
| PATENT NO. | : 7,488,070 B2 |
| APPLICATION NO. | : 11/472030 |
| DATED | : February 10, 2009 |
| INVENTOR(S) | : Christoph Hauger and Peter Reimer |

It is certified that error appears in the above-identified patent and that said Letters Patent is hereby corrected as shown below:

On the Title Pg Item (56) References Cited, Other Publications:

Change "Roorda, A., et al., "Adaptive Optics Scanning Laser Opthalmoscopy", Optics Express, vol" to --Roorda, A., et al., "Adaptive Optics Scanning Laser Ophthalmoscopy", Optics Express, vol.--

On the Title Pg Item (56) Page 2, under heading Foreign Patent Documents:

Change "DE 101 57 942 A1" to --DE 101 57 842 A1--

Column 4, line 22:

Change "... a retain 3a ..." to --... a retina 3a ...--

Column 4, line 38:

Change "... 37 MacArthur Ave., Devens, Mass. 01432 ..." to --37 MacArthur Ave., Devens, MA 01432--

Column 6, line 3:

Change "951 of the retina 3a." to --$95_1$ of the retina 3a.--

UNITED STATES PATENT AND TRADEMARK OFFICE
CERTIFICATE OF CORRECTION

PATENT NO. : 7,488,070 B2
APPLICATION NO. : 11/472030
DATED : February 10, 2009
INVENTOR(S) : Christoph Hauger and Peter Reimer It is certified that error appears in the above-identified patent and that said Letters Patent is hereby corrected as shown below:

Column 8, line 43:

Change "... of these measurement is improved ..." to --... of these measurements is improved ...--

Signed and Sealed this

Thirtieth Day of June, 2009

JOHN DOLL
*Acting Director of the United States Patent and Trademark Office*